US00PP28544P3

(12) United States Plant Patent
Burkitt

(10) Patent No.: US PP28,544 P3
(45) Date of Patent: Oct. 24, 2017

(54) APPLE TREE NAMED 'JIVE'

(50) Latin Name: ***Malus* Mill.**
Varietal Denomination: Jive

(71) Applicant: Edward Mark Burkitt, Hastings (NZ)

(72) Inventor: Edward Mark Burkitt, Hastings (NZ)

( * ) Notice: Subject to any disclaimer, the term of this patent is extended or adjusted under 35 U.S.C. 154(b) by 291 days.

(21) Appl. No.: 14/544,113

(22) Filed: Nov. 24, 2014

(65) Prior Publication Data

US 2015/0163974 P1 Jun. 11, 2015

Related U.S. Application Data

(60) Provisional application No. 61/913,043, filed on Dec. 6, 2013.

(51) Int. Cl.
*A01H 5/08* (2006.01)

(52) U.S. Cl.
USPC ..... Plt./161

(58) Field of Classification Search
USPC ..... Plt./161
CPC ..... A01H 5/0875
See application file for complete search history.

(56) References Cited

PUBLICATIONS

GTITM UPOVROM Citation for 'Jive' as per NZ PBR APP162; Aug. 24, 2004; 1 page.*

* cited by examiner

*Primary Examiner* — Kent L Bell
(74) *Attorney, Agent, or Firm* — Michelle Bos Legal LLC

(57) ABSTRACT

A new and distinct apple tree is disclosed. 'Jive', a limb sport of 'GS48', is notable for its distinctive fruit, which exhibits a red coloration, with strong defined striping present.

2 Drawing Sheets

Latin name of the genus and species of the plant claimed: *Malus* Mill.

Variety denomination: 'Jive'.

STATEMENT REGARDING FEDERALLY SPONSORED RESEARCH OR DEVELOPMENT

None.

BACKGROUND OF THE INVENTION

The new apple cultivar originated as a spontaneous limb sport mutation of 'GS48' (unpatented). It was discovered by the inventor in March 2001 in a cultivated orchard at Pakowhai, New Zealand. 'Jive' was asexually propagated by budding at Pakowhai, New Zealand in 2001, and has been shown to remain true to type over successive generations.

BRIEF SUMMARY OF THE INVENTION

'Jive' is a new and distinct apple tree notable for its distinctive fruit, which exhibits a red coloration.

BRIEF DESCRIPTION OF THE PHOTOGRAPH

Figure 1:
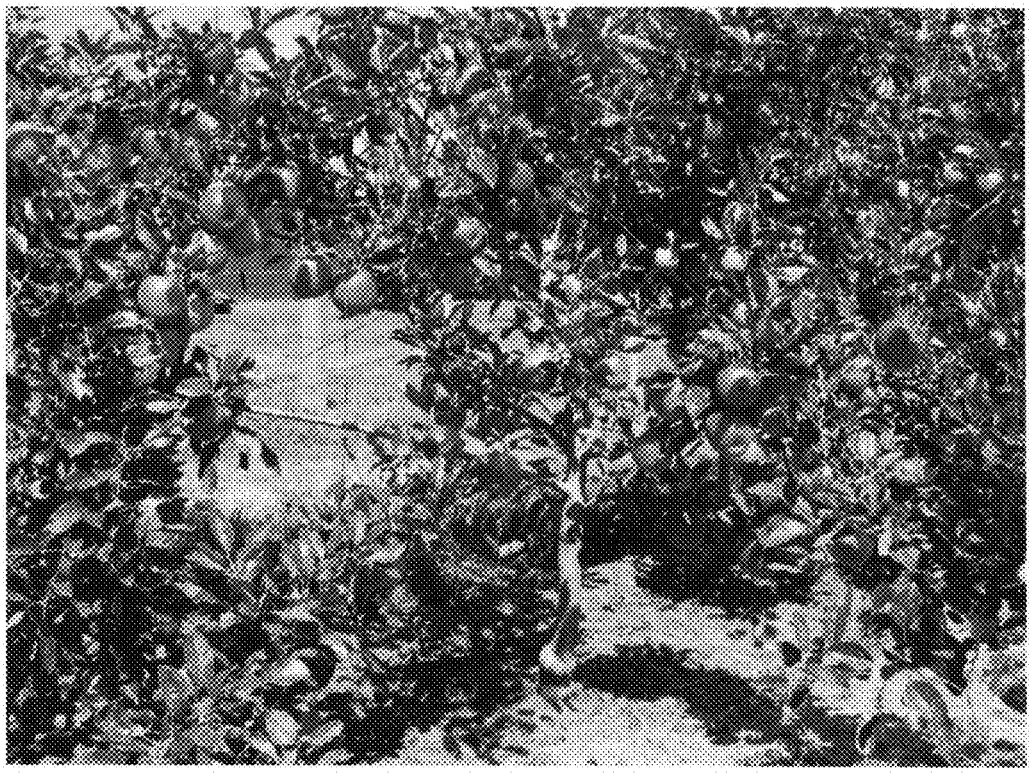
Figure 2:
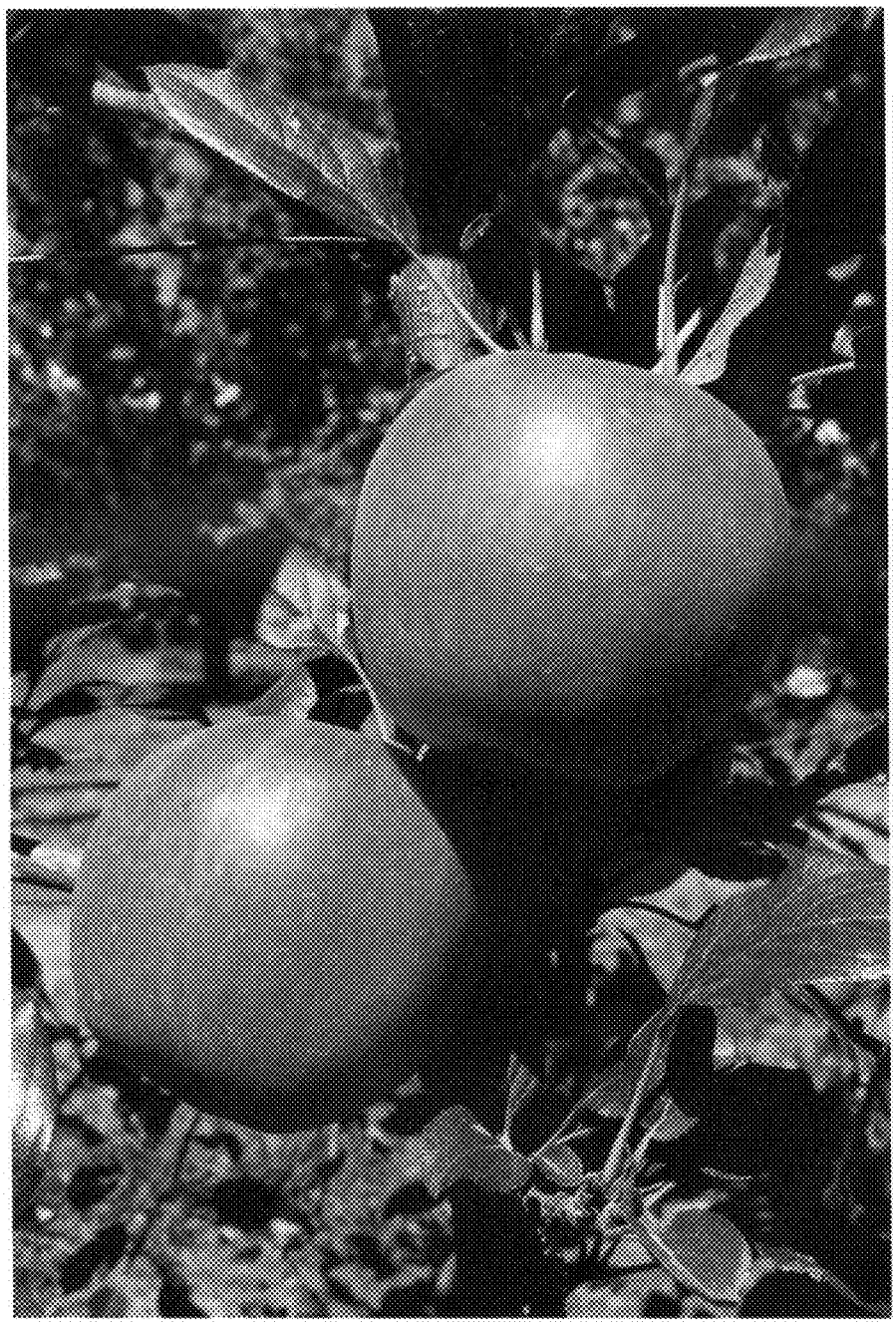

FIG. 1 shows the tree and fruit of the new cultivar; and FIG. 2 shows the fruit and leaves of the new cultivar.

DETAILED BOTANICAL DESCRIPTION

The following detailed botanical description is based on observations made during the 2006/2007 and 2017 growing seasons at Pakowhai, New Zealand, and in 2017 near Wapato, Wash. All colors are described according to The Royal Horticultural Society Colour Chart ($4^{th}$ edition, 2001). It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:

*Vigor*.—Medium-Strong.
*Habit*.—Upright.
*Type*.—Ramified.
*Height*.—3 m.
*Spread*.—1.5 m.
*Trunk diameter*.—3 cm at 30 cm above graft.
*Bark*.—Smooth with rough lenticels, grey 201D.
*Lenticels*.—4 per $cm^2$; oblong, 1 mm×5 mm; black 202D.
*Winter hardiness*.—Hardy in area tested (USDA Zone 6-7).

Branches:

*Length*.—1.5 to 2 m.
*Diameter*.—About 2.5 cm at 1 m from trunk.
*Color*.—Grey 201D.
*Lenticels*.—3 to 5 per $cm^2$; oblong, 1 mm wide by 2 to 3 mm long; black 202D.
*Crotch angle*.—Nearly horizontal, about 75°.

Dormant one year old shoot:

*Lenticels*.—5 to 7 per $cm^2$; round, 1 mm diameter; yellow 11D.
*Color*.—Brown 200C.

*Pubescence*.—Medium to strong; brown 200C.
*Thickness* (*center diameter of middle internode*).—Medium.
*Internode length*.—Medium.

Flower buds:
*Quantity per spur*.—4 to 5.
*Bud shape*.—Elongated.
*Apex*.—Pointed.
*Length*.—1 cm.
*Diameter*.—0.5 cm
*Color at balloon stage*.—Red-purple 63A.

Flower:
*Diameter of open flower*.—3.5 cm.
*Relative position of margins*.—Overlapping.
*Date of first bloom*.—September 13$^{th}$ in Pakowhai NZ; April 22 in Wapato, Wash.
*Date of full bloom*.—September 22$^{nd}$ in Pakowhai NZ; April 26 in Wapato, Wash.

Petals:
*Quantity per flower*.—5.
*Shape*.—Obovate.
*Apex*.—Rounded.
*Base*.—Cuneate.
*Length*.—2 cm.
*Width*.—1.2 cm.
*Margin*.—Ruffled.
*Color of upper surface*.—Red 62A and white N155C.
*Color of lower surface*.—Red 62C and white N155C.
*Sepals*.—5 per flower; length 1.5 cm, width 0.4 cm; lanceolate with pointed tip; smooth margins; yellow-green 146D.
*Pedicel*.—Length 2 cm, diameter 1 mm; yellow-green 146D.

Reproductive organs:
*Pistils*.—Length 1.1 cm; yellow-green 151B.
*Anthers*.—About 18 per flower; length 1 mm.
*Pollen color*.—Yellow 2C.
*Stigma*.—Length 1 mm; yellow-green 151B.
*Style*.—Length 1 cm; yellow-green 151B.
*Ovary*.—Length 4 mm; green 143A.

Leaf:
*Length*.—Short to Medium, 68 to 81 mm.
*Width*.—Medium, 32 to 41 mm.
*Shape*.—Elliptical.
*Apex*.—Cuspidate.
*Base*.—Cuneate.
*Shape of margins*.—Serrate.
*Color of upper surface*.—Yellow-green 146B.
*Color of lower surface*.—Yellow-green N144D.
*Attitude in relation to shoot*.—Upwards.

Petiole:
*Petiole length*.—Medium to long; Average 34 mm.
*Diameter*.—1 mm.
*Color*.—Yellow-green 145C.

Fruit:
*Quantity per cluster*.—2 to 3 after thinning.
*Size*.—Large; 219 gm.
*Height*.—72.6 mm.
*Diameter*.—74.4 mm.
*Ratio: height/width*.—Very large; 0.98.
*Shape*.—Globose to obloid.
*Ribbing*.—Absent.
*Crowning at calyx end*.—Moderate.
*Aperture of eye*.—Closed.
*Depth of eye basin*.—Deep; 11.4 mm.
*Width of eye basin*.—Broad; 31.6 mm.
*Thickness of stalk*.—Medium, about 3 mm.
*Length of stalk*.—Short to medium, about 12 mm.
*Depth of stalk cavity*.—Deep; 15.6 mm.
*Width of stalk cavity*.—Broad; 33.8 mm.
*Greasiness of skin*.—Absent or very weak.
*Ground color of skin*.—Yellow 8B.
*Amount of overcolor of skin*.—Large, 50 to 75%.
*Color of overcolor of skin*.—Red 50A.
*Intensity of overcolor*.—Medium.
*Pattern of overcolor*.—Solid flush with strongly defined stripes.
*Flesh texture*.—Medium.
*Juiciness*.—Medium to high.
*Brix*.—13° to 16°.
*Flesh color*.—Cream 155D.
*Aroma*.—Faint, sweet.
*Locules*.—7 per fruit; length 10 mm, width 5 mm.
*Seeds*.—7 to 9 per fruit; teardrop shape; length 7 to 8 mm, width 4 mm; brown 200B.
*Eating quality*.—Excellent.

Harvest:
*Amount of fruit produced per tree per harvest*.—Highly productive.
*Harvest date range*.—Early to late March in Pakowhai, NZ.

Diseases/pests:
*Susceptibility*.—Low susceptibility to powdery mildew.

Market use: Fresh market.

I claim:

1. A new and distinct apple tree substantially as shown and described herein.

* * * * *